(12) United States Patent
Hoenes et al.

(10) Patent No.: US 7,439,080 B2
(45) Date of Patent: Oct. 21, 2008

(54) METHOD FOR DETERMINING THE GLUCOSE CONCENTRATION BY FLUORESCENCE POLARIZATION

(75) Inventors: Joachim Hoenes, Zwingenberg (DE); Herbert von der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 225 days.

(21) Appl. No.: 11/277,313

(22) Filed: Mar. 23, 2006

(65) Prior Publication Data

US 2006/0216773 A1 Sep. 28, 2006

(30) Foreign Application Priority Data

Mar. 23, 2005 (EP) ................... 05006451

(51) Int. Cl.
*G01N 33/544* (2006.01)
*G01N 21/76* (2006.01)
(52) U.S. Cl. ...................... 436/529; 436/172
(58) Field of Classification Search ....... None
See application file for complete search history.

(56) References Cited

U.S. PATENT DOCUMENTS

| | | | | |
|---|---|---|---|---|
| 5,593,852 | A * | 1/1997 | Heller et al. | 435/14 |
| 5,660,991 | A | 8/1997 | Lakowicz et al. | |
| 6,596,546 | B1 | 7/2003 | Jolley et al. | |
| 2002/0058863 | A1* | 5/2002 | Petersson et al. | 600/310 |

FOREIGN PATENT DOCUMENTS

WO WO 02/03855 A1 1/2002

OTHER PUBLICATIONS

Ballerstadt et al. A Fluorescence Affinity Hollow Fiber Sensor for Continuous Transdermal Glucose Monitoring; Analytical Chemistry, vol. 72, No. 17 (2000) pp. 4185-4192.*
XP-002321003—U. Beyer et al., "Recording of subcutaneous glucose dynamics by a viscometric affinity sensor", *Diabetologia*, vol. 44, p. 416-423 (2001).
Lydia J. McCartney et al., "Near-Infrared Fluorescence Lifetime Assay for Serum Glucose Based on Allophycocyanin-Labeled Concanavalin A", *Analytical Biochemistry*, vol. 292, p. 216-221 (2001).
Rudolf Ehwald et al., "Viscosimetric Affinity Assay", *Analytical Biochemistry*, vol. 234, p. 1-8 (1996).
Zongping Xia et al., "Reliable and Global Measurement of Fluorescence Resonance Energy Transfer Using Fluorescence Microscopes", *Biophysical Journal*, vol. 81, p. 2395-2402, (Oct. 2001).
Gerald W. Gordon et al. "Quantitative Fluorescence Resonance Energy Transfer Measurements Using Fluorescence Microscopy", *Biophysical Journal*, vol. 74, p. 2702-2713 (May 1998).
M.E. Jolley, "Fluorescence Polarization Immunoassay for the Determination of Therapeutic Drug Levels in Human Plasma", *Journal of Analytical Toxicology*, vol. 5, p. 236-240, (Sep./Oct. 1981).
Mohammad Sarwar Nasir et al., "Fluorescence Polarization: An Analytical Tool for Immunoassay and Drug Discovery", *Combinatorial Chemistry & High Throughput Screening*, vol. 2, p. 177-190 (1999).
B. Rangarajan et al., "Review: Characterization of hydrogels using luminescence spectroscopy", *Biomaterials*, vol. 17, p. 649-661 (1996).
M. Francis Perrin, "Polarisation de la lumiere de fluorescence. Vie moyenne des molecules dans l'etat excite", *Journal de Physique*, No. 12, p. 390-401 (1926).

* cited by examiner

*Primary Examiner*—Jon P Weber
*Assistant Examiner*—Paul C. Martin
(74) *Attorney, Agent, or Firm*—Justin L. Sage; Roche Diagnostics Operations, Inc.

(57) ABSTRACT

The invention generally relates to a method for in vivo glucose monitoring in which the glucose concentration is measured by means of fluorescence polarization by detecting the change in viscosity, caused by changes in the glucose concentration.

9 Claims, No Drawings

METHOD FOR DETERMINING THE GLUCOSE CONCENTRATION BY FLUORESCENCE POLARIZATION

REFERENCE TO RELATED APPLICATIONS

The present application is a based on and claims priority to European Patent Application No. 05 006 451.8, filed Mar. 23, 2005 which is hereby incorporated by reference in its entirety.

TECHNICAL FIELD

The invention generally relates to a method and system for in vivo glucose monitoring in which the glucose concentration is measured by means of fluorescence polarization.

BACKGROUND AND SUMMARY

Fluorescence polarization is a known powerful method for the rapid and homogeneous analysis of molecular interactions in biological and chemical systems.

The principles of fluorescence polarization are based on the excitation of a fluorescent molecule, the fluorophore, with polarized light. This results in the emission of photons in the plane which is parallel and perpendicular to the excitation plane and yields information about the local environment of the fluorophore.

The rotation of fluorophores in solution can be observed by measuring the rotation of the plane of polarization of the light that was originally beamed in.

The polarization value for solved randomly oriented molecules is between 0 and 0.5 depending on the rotational speed of the molecules during the fluorescence lifetime of the excited state. If the rotation is rapid in comparison with the fluorescence lifetime, the polarization of the emitted radiation is almost zero. If, in contrast, the rotation is slow compared to the fluorescence lifetime, the polarization in the emitted light is high. Small molecules rotate rapidly and therefore have a smaller polarization value. Conversely larger molecules have a higher polarization value due to their slow rotation.

One of the advantage of fluorescence polarization is that variations in the intensity in the optical system and in the sample solution are automatically eliminated by relating the various polarized emission components to one another. Hence errors caused by the optical system or by inconsistent samples e.g. samples that absorb to different extents, do not usually occur with this method.

The observed rotation depends on the rotation relaxation time and is only influenced by the temperature, the viscosity and the molecular weight of the fluorophore. Thus fluorescence polarization is a suitable method for measuring these parameters and in particular changes in these parameters.

The use of static and dynamic fluorescence polarization to diagnostically detect complexation reactions is know in prior art. In this method an antigen that is labelled with a fluorophore and is present in solution is reacted with an antibody which is present in a diluted serum sample in order to form an immune complex. The immune complex is then detected by the change in fluorescence polarization.

It is also known that fluorescence polarization is used as an analytical tool for immunoassays e.g. to detect serum proteins, antibodies and hormones, to detect toxins in seeds and for drug detection.

In such tests one generally uses fluorescently-labelled antigens or antibodies whose polarization is measured. Their reaction with a specific antibody or antigen results in an increase in fluorescence polarization i.e. after an antigen-antibody complex has been formed which increases the effective molecular weight.

The application of fluorescence polarization as a tool for investigating polyelectrolyte complexes and hydrogels is also known. In this method the fluorophore is covalently linked with the polymer to be examined.

A disadvantage of the known diagnostic methods in which fluorescence polarization is measured, is that a laborious optimization of the label i.e. of the fluorophore and of its binding to the antigen or antibody is required to prevent an impairment of the actual complex formation. Furthermore labels that are to be used to detect changes in molecular weight by fluorescence polarization have to be bound covalently to the labelled molecule since even small relative movements reduce the fluorescence polarization and thus the effective signal.

The fluorescence resonance energy transfer (FRET) method is another analytical method in which fluorophores are used. In the FRET method photon energy is transferred in a non-radiative manner from an excited fluorophore (the donor) to another fluorophore (the acceptor) when the distance between the two of them is no more than 1-10 nm. This energy transfer occurs non-radiatively, essentially by a dipole/dipole interaction. The FRET method can also be used for example to detect molecular interactions between two protein partners or structural changes within a molecule.

However, a disadvantage of the FRET method is that only certain fluorophore pairs are suitable for the FRET method since, as apart from other prerequisites such as dipole orientation and adequate fluorescence lifetime, the emission spectrum of the donor must overlap with the excitation spectrum of the acceptor. Two labels are necessary which is why the FRET method is even more complicated than fluorescence polarization.

Various methods are known from the prior art for detecting glucose. One such method is the detection of glucose by means of the complexation reaction concanavalin A (ConA)-dextran. Glucose interferes with the complex formation which results in a change in viscosity. Hence the complex formation and a change thereof and thus the concentration of glucose can be measured by means of viscosimetry. A disadvantage of this method for detecting glucose is that the viscosimetric method is technically very complicated.

Another method for determining glucose is based on the FRET method. In this method, Concanavalin A and dextran can both be labelled with a fluorophore. The label results in an effective energy transfer from the first to the second fluorophore (FRET) in the complex during complex formation. The addition of glucose leads to a dissolution of the complex which decreases the intensity of the radiation from the second fluorophore. A major disadvantage of detecting glucose using the FRET method is that concanavalin A as well as dextran have to be labelled with a fluorophore. Moreover, the corresponding fluorophores must have suitable fluorescence properties. Reabsorption of the radiation emitted from the first fluorophore by the second fluorophore also reduces the effective signal since it also occurs without complex formation.

In addition to the methods described above, several methods methods are known for continuously monitoring glucose in vivo and in vitro> For example microdialysis and enzymatic detection outside the body; viscosimetry using concanavalin A/dextran (GlucOnline®); electrochemical sensors employing an enzymatic conversion of the glucose in the body (Minimed®); long-term sensors which for example operate according to the FRET method on the basis of labelled concanavalin A and dextran, have all been used to detect glucose.

However, no method or system is known in which an in vivo glucose monitoring for determining the glucose concentration or an in vitro determination of the glucose concentration can be carried out by means of fluorescence polarization.

Therefore, an object of the invention is to overcome the disadvantages of the prior art and to provide a simple and accurate method for in vivo glucose monitoring by means of fluorescence polarization as well as a system which can be used in a method for in vivo glucose monitoring.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

DETAILED DESCRIPTION

A method for in vivo glucose monitoring in an individual is achieved by implantation of a container into the skin of an individual. The container is permeable to glucose. In addition the container has an inner space which contains a mixture of a glucose-binding lectin, preferably concanavalin A, dextran and a probe consisting of a fluorophore and a carrier, and a sensor for measuring the fluorescence polarization. The glucose concentration is measured by detecting a change in viscosity in the inner space of the container by means of fluorescence polarization.

In order to create a system that can be implanted in an individual, the container is first filled with a mixture comprising a glucose-binding lectin, preferably concanavalin A, dextran and a probe consisting of a fluorophore and a carrier. The container is then closed or sealed. The sealed container is then operatively connected with a sensor which is preferably a light guide in order to beam light in and out. The resulting system is them implanted under the skin and the glucose concentration is measured by detecting the viscosity change by means of fluorescence polarization.

The container used in the method according to the invention contains a mixture of a lectin-dextran complex, preferably of a concanavalin A-dextran complex, and a probe. The polarization value of this mixture is measured by the sensor using the probe which contains a fluorophore. After the container is implanted in the body of an individual, glucose diffuses from body fluids, in particular from blood or through the cytoplasm, into the container. Glucose has an effect on the lectin-dextran complex formation and preferably on the concanavalin A-dextran complex formation. This results in a change in the viscosity of the mixture contained in the container. This change in viscosity causes a change in the fluorescence polarization of the fluorophore present in the mixture such that a change in the concentration of glucose can be determined by measuring the polarization value. The glucose concentration is preferably determined continuously.

The method according to the invention can be used to monitor D-glucose and L-glucose in vivo. It is preferably used to monitor D-glucose in vivo.

Hence the method according to the invention differs from the known prior art methods in that neither the glucose-binding lectin nor dextran has to be labelled with a fluorophore. Moreover, the change in viscosity of the mixture is detected and not the change in molecular weight.

In the method according to the invention the formation of the complex of glucose-binding lectin and dextran, and in particular of concanavalin A and dextran is not disturbed by the probe. Other substances only interfere if, like glucose, they bind to the lectin and in particular to concanavalin A. Such substances usually only occur in the human body at low concentrations.

The probe can be selected with regard to simple instruments. Moreover, the method allows the use of simpler instruments compared to the FRET method and to viscosimetry; thus the entire fluidic system (pumps, tubes) can be dispensed with in the method according to the invention.

The method and the system of the present invention can be used for continious monitoring of the glucose concentration for a longer time compared to conventional enzyme-based methods for continuous glucose monitoring. Since in this method no enzymatic reaction takes place and as a result of which the method is suitable for a longer period of use. Moreover, no diffusion barriers are required to minimize interferences since no undesired reaction occurs with products.

Suitable containers for carrying out the method according to the invention are flexible or rigid containers made of physiologically compatible materials which are permeable to glucose and impermeable to the glucose-binding lectin and in particular to concanavalin A, dextran and the probe. In particular containers made of semipermeable membranes known in the literature such as cellulose and/or cellulose derivatives, polyamide and/or polyamide derivatives, polysulfones and/or polysulfone derivatives come into consideration. A small membrane sachet made of regenerated cellulose is particularly preferably used.

The exclusion limit of the membrane should be selected such that the glucose-binding lectin, preferably concanavalin A, dextran and the fluorescently labelled probe cannot pass through it. Preferred exclusion limits are <100 kDa, preferably <50 kDa and particularly preferably 10-20 kDa.

Glucose-binding lectins in particular concanavalin A and dextran are known and commercially available; they are mixed by conventional methods and thereby optionally dissolved in a diluent such as a conventional buffer solution.

Dextran having an average molecular weight of 10 kDa to 1000 kDa, preferably of 20 kDa to 500 kDa and particularly preferably of 100 kDa to 200 kDa comes into consideration for carrying out the method according to the invention.

All glucose-binding lectins such as concanavalin A (ConA), Lens culinaris agglutinin and pea lectin-I (PSA) come into consideration for carrying out the method according to the invention. Concanavalin A is particularly preferably used in the method according to the invention.

The container can alternatively contain other complexation systems whose complex formation is influenced by glucose, such as dextran and other glucose-binding proteins.

A particular measuring range can be adjusted by the concentration of glucose-binding lectin and dextran and in particular of concanavalin A and dextran.

The concentration of the glucose-binding lectin and in particular of concanavalin A is preferably 0.2-5%, preferably 0.5-2% and particularly preferably 0.5-1%.

The concentration of dextran is 1-20%, preferably 3-10% and particularly preferably 5-8%.

The probe consists of a fluorophore and a carrier. The fluorophore and the carrier should be covalently linked.

Fluorophores which preferably come into consideration for carrying out the method according to the invention are all fluorophores which have a fluorescence lifetime between 10 and 1000 ns, preferably >100 ns and a wavelength of 400 to 800 nm. The fluorophores must be long-lived in order to be adequately sensitive to viscosity-dependent changes with the relatively long rotation correlation time of the carrier. Hence transition metal complexes such as ruthenium tris-bipyridyl derivatives come primarily into consideration. They are also commercially available as isothio-cyanates or N-hydroxysuccinimide esters and can thus be used directly to label the carrier. Bis-(bipyridine)-5-(isothiocyanato-phenanthroline)-Ru(PF$_6$)$_2$ is particularly preferably used.

Physiologically compatible polymers such as organic polymers e.g. polyethylene or polyethylene copolymers and biopolymers such as polypeptides and proteins such as serum albumin come into consideration as carriers. Proteins are particularly preferably used. Carriers which do not or do not significantly bind to the glucose-binding lectin and in particular to concanavalin A, dextran and/or the concanavalin A/dextran complex under the conditions of the method are particularly preferably used to carry out the method according to the invention. This is usually the case for proteins.

The molecular weight of the probe consisting of the fluorophore and the carrier must be of such a magnitude that the probe cannot diffuse out of the bag. The molecular weight of the probe can for example be in the range of 20 kDa to 500 kDa.

Very small amounts of probe are used to carry out the method according to the invention. The amount is determined by the sensitivity of the measuring set-up.

Optical sensors such as light guides, for example quartz or glass fibres or light-conducting polymers come into special consideration as sensors for measuring the fluorescence polarization in order to carry out the method according to the invention.

The term individual encompasses any warm-blooded animal and in particular includes mammals such as humans and non-human primates such as chimpanzees and other monkey and anthropoid ape species; farm animals such as cows, sheep, pigs, geese and horses; domestic animals such as dogs and cats; laboratory animals for example rodents such as mice, rats and guinea pigs and suchlike. Male or female adults, children and newborns should be included.

The container is implanted in the body of an individual by conventional methods such as by puncturing. The container is preferably implanted under the skin. The container can be implanted in all suitable parts of the body, preferably in the arm or under the abdominal skin. The glucose concentration is measured intermittently or continuously, preferably continuously.

Another subject matter of the present invention is a technically simple system for in vivo glucose monitoring in which the formation of the complex of a glucose-binding lectin and dextran, in particular concanavalin A and dextran is not disturbed by its labelling with a fluorophore.

Another subject matter of the present invention is the use of the system described above in a method for intermittently or continuously monitoring glucose in vivo and preferably for continuous glucose monitoring.

Another subject matter of the present invention is a diagnostic composition containing a glucose-binding lectin, preferably concanavalin A, dextran and a probe as well as the use of a mixture containing a glucose-binding lectin, preferably concanavalin A, dextran and a probe to produce a diagnostic agent.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for in vivo glucose monitoring in an individual, the method comprising:
    filling a container that is permeable to glucose and having an inner space with a mixture containing a glucose-binding lectin and a probe;
    sealing the container;
    operatively coupling the container with a sensor, wherein the sensor is for measuring the fluorescence polarization;
    implanting the container and the operatively coupled sensor into the individual; and
    measuring the glucose concentration by detecting a change in viscosity in the inner space of the container by means of fluorescence polarization.

2. The method according to claim 1, wherein the glucose-binding lectin is concanavalin A or dextran.

3. The method according to claim 1, wherein the probe comprises a fluorophore and a carrier.

4. The method according to claim 3, wherein a protein is used as the carrier.

5. The method according to claim 3, wherein the fluorophore is a long-lived fluorophore with a fluorescence lifetime of >100 ns.

6. The method according to claim 1, wherein the container is made of a semipermeable membrane selected from the group consisting of cellulose, cellulose derivatives, polyamide, polyamide derivatives, polysulfones and polysulfone derivatives.

7. The method according to claim 1, wherein the sensor comprises a light guide capable of beaming light in or out.

8. The method according to claim 1, wherein the determination of the glucose concentration is carried out continuously.

9. The method according to claim 1, the molecular weight of the probe is adjusted such that the probe cannot diffuse out of the container.

* * * * *